United States Patent
Beh

(10) Patent No.: US 12,033,366 B2
(45) Date of Patent: Jul. 9, 2024

(54) MATCHING APPARATUS, MATCHING METHOD, AND MATCHING PROGRAM

(71) Applicant: FUJIFILM Corporation, Tokyo (JP)

(72) Inventor: Teck Chuan Beh, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 353 days.

(21) Appl. No.: 17/505,632

(22) Filed: Oct. 20, 2021

(65) Prior Publication Data

US 2022/0044052 A1 Feb. 10, 2022

Related U.S. Application Data

(63) Continuation of application No. PCT/JP2020/011576, filed on Mar. 17, 2020.

(30) Foreign Application Priority Data

May 28, 2019 (JP) .................. 2019-099177

(51) Int. Cl.
*G06T 7/00* (2017.01)
*G06F 18/22* (2023.01)
(Continued)

(52) U.S. Cl.
CPC ............ *G06V 10/443* (2022.01); *G06F 18/22* (2023.01); *G06T 7/0014* (2013.01); *G06T 7/74* (2017.01); *G06T 2207/20224* (2013.01)

(58) Field of Classification Search
CPC . G06T 2207/10072; G06T 2207/10116; G06T 7/0012; G06T 7/0016; G06T 7/33;
(Continued)

(56) References Cited

U.S. PATENT DOCUMENTS

| 8,194,947 B2 * | 6/2012 | Zingaretti ............. G06T 7/0012 |
| | | 382/128 |
| 10,980,493 B2 * | 4/2021 | Osawa .................... G06T 15/08 |

(Continued)

FOREIGN PATENT DOCUMENTS

| JP | 2009160045 | 7/2009 |
| JP | 2011177494 | 9/2011 |

(Continued)

OTHER PUBLICATIONS

"International Search Report (Form PCT/ISA/210) of PCT/JP2020/011576," mailed on Jun. 2, 2020, with English translation thereof, pp. 1-5.

(Continued)

*Primary Examiner* — Li Liu
(74) *Attorney, Agent, or Firm* — JCIPRNET

(57) ABSTRACT

A reference part extracting unit extracts at least one reference part that is common in a first image and a second image, from each of the first image and the second image. A first position information deriving unit derives first position information indicating a relative position of at least one abnormal part specified in the first image, relative to the at least one reference part in the first image. A second position information deriving unit derives second position information indicating a relative position of at least one abnormal part specified in the second image, relative to the at least one reference part in the second image. A matching unit associates, on the basis of a difference between the first position information and the second position information, the abnormal part included in the first image and the abnormal part included in the second image with each other.

13 Claims, 10 Drawing Sheets

(51) Int. Cl.
  *G06T 7/73* (2017.01)
  *G06V 10/44* (2022.01)
(58) Field of Classification Search
  CPC . G06T 2207/30004; G06T 2207/30012; G06T 7/00; G06T 7/62; G06T 7/70; G06T 7/74; G06T 2200/24; G06T 2207/30008; G06T 7/0014; G06T 7/60; G06V 10/443; G06V 10/764
  See application file for complete search history.

(56) References Cited

U.S. PATENT DOCUMENTS

| | | | | |
|---|---|---|---|---|
| 11,317,896 | B2* | 5/2022 | Abe | A61B 8/543 |
| 11,373,361 | B2* | 6/2022 | Nempont | A61B 8/461 |
| 2011/0190633 | A1 | 8/2011 | Kawagishi et al. | |
| 2016/0314587 | A1* | 10/2016 | Ishikawa | G16H 50/20 |
| 2016/0335777 | A1* | 11/2016 | Borsdorf | G06T 7/0012 |
| 2019/0000318 | A1* | 1/2019 | Caluser | A61B 5/0073 |
| 2019/0005660 | A1 | 1/2019 | Kinoshita et al. | |
| 2020/0184649 | A1* | 6/2020 | Wang | A61B 5/7275 |

FOREIGN PATENT DOCUMENTS

| | | | |
|---|---|---|---|
| JP | 2013123528 | * | 6/2013 |
| JP | 2019013724 | | 1/2019 |

OTHER PUBLICATIONS

"Written Opinion of the International Searching Authority (Form PCT/ISA/237)" of PCT/JP2020/011576, mailed on Jun. 2, 2020, with English translation thereof, pp. 1-8.

* cited by examiner

MATCHING APPARATUS, MATCHING METHOD, AND MATCHING PROGRAM

CROSS-REFERENCE TO RELATED APPLICATIONS

This application is a Continuation of PCT International Application No. PCT/JP2020/011576 filed on Mar. 17, 2020, which claims priority under 35 U.S.C § 119(a) to Japanese Patent Application No. 2019-099177 filed on May 28, 2019. Each of the above application(s) is hereby expressly incorporated by reference, in its entirety, into the present application.

BACKGROUND OF THE INVENTION

1. Field of the Invention

The present disclosure relates to a matching apparatus, a matching method, and a matching program that cause abnormal parts to match between images, the abnormal parts being included in images that are acquired for a photographic subject at different imaging times.

2. Description of the Related Art

In recent years, the progress of medical equipment such as a CT (Computed Tomography) apparatus and an MRI (Magnetic Resonance Imaging) apparatus has enabled an increasing use of a high-quality high-resolution three-dimensional image in image diagnosis. In addition, an image is analyzed by CAD (Computer-Aided Diagnosis), an abnormal part such as a tumor is extracted, and the size, type, and the like of the abnormal part are acquired as analysis results. The use of such analysis results can reduce the load on an X-ray interpreter who interprets a medical image.

On the other hand, to make a diagnosis on a recovery status or a progress status of a disease, in some cases, over-time comparison observation using a previous medical image of the same patient is performed. For example, in a case of follow-up of a tumor in a liver, three-dimensional images of the abdomen at different imaging times are displayed in a juxtaposed manner, and the displayed two three-dimensional images are viewed to check how the tumor has changed over time.

In a case of over-time comparison observation in this manner, positions of abnormal parts, such as a tumor included in the images, need to be associated with each other, that is, matching needs to be performed. For matching, three-dimensional images at different imaging times need to be aligned. As a method of an alignment method, a method such as rigid body alignment or non-rigid-body alignment is used. In addition, as a method for image alignment, for example, the method described in JP2009-160045A is also proposed. The method described in JP2009-160045A is a method of selecting, from among a plurality of feature points extracted from each of two three-dimensional images, a plurality of sets of feature points that are associated between the images, and of specifying corresponding sections in the two three-dimensional images by using position information of each of the selected plurality of sets of feature points.

However, in rigid body alignment and non-rigid-body alignment, and further, the method described in JP2009-160045A, since the calculation amount is large, processes need a long time. In addition, with these methods, between medical images acquired by different imaging methods, such as a medical image captured by a CT apparatus and a medical image captured by an MRI apparatus, the alignment accuracy may decrease. Thus, with these methods, it is unlikely to perform matching of abnormal parts between images accurately.

The present disclosure has been made in view of the above circumstances and is directed at enabling, between images at different imaging times, matching of abnormal parts included in the images accurately with a small calculation amount.

SUMMARY OF THE INVENTION

A matching apparatus according to the present disclosure includes:
a reference part extracting unit that extracts at least one reference part that is common in a first image and a second image, from each of the first image and the second image, the first image and the second image being images of a photographic subject at different imaging times;
a first position information deriving unit that derives first position information indicating a relative position of at least one abnormal part specified in the first image, relative to the at least one reference part in the first image;
a second position information deriving unit that derives second position information indicating a relative position of at least one abnormal part specified in the second image, relative to the at least one reference part in the second image; and
a matching unit that associates, on the basis of a difference between the first position information and the second position information, the abnormal part included in the first image and the abnormal part included in the second image with each other.

"Reference part" means a part whose position, size, shape, and the like do not change over time. For example, a bone may be used as the reference part.

Note that, in the matching apparatus according to the present disclosure, the first position information deriving unit may derive, as the first position information, a vector from the reference part toward the abnormal part included in the first image, and the second position information deriving unit may derive, as the second position information, a vector from the reference part toward the abnormal part included in the second image.

In addition, in the matching apparatus according to the present disclosure, on the basis of the first position information and the second position information, the matching unit may derive, as the difference, a distance between the abnormal part included in the first image and the abnormal part included in the second image.

In addition, in the matching apparatus according to the present disclosure, the matching unit may associate the abnormal part included in the first image and the abnormal part included in the second image with each other for which the difference is less than a predetermined threshold.

In addition, in the matching apparatus according to the present disclosure, the reference part extracting unit may extract a plurality of reference parts.

In addition, in the matching apparatus according to the present disclosure, the reference part may be a bone, and, in particular, may be a vertebra.

In addition, the matching apparatus according to the present disclosure may further include an abnormal part extracting unit that extracts the at least one abnormal part from each of the first image and the second image.

In addition, the matching apparatus according to the present disclosure may further include a size changing unit that makes a size of the reference part included in the first image and a size of the reference part included in the second image correspond to each other in a case where the size of the reference part included in the first image and the size of the reference part included in the second image are different from each other.

In addition, the matching apparatus according to the present disclosure may further include a display control unit that displays, on a display unit, the first image and the second image in which the associated abnormal parts are emphasized.

A matching method according to the present disclosure includes:

extracting at least one reference part that is common in a first image and a second image, from each of the first image and the second image, the first image and the second image being images of a photographic subject at different imaging times;

deriving first position information indicating a relative position of at least one abnormal part specified in the first image, relative to the at least one reference part in the first image;

deriving second position information indicating a relative position of at least one abnormal part specified in the second image, relative to the at least one reference part in the second image; and associating, on the basis of a difference between the first position information and the second position information, the abnormal part included in the first image and the abnormal part included in the second image with each other.

Note that it is possible to provide a non-transitory computer readable recording medium storing a program causing a computer to execute the matching method according to the present disclosure.

Another matching apparatus according to the present disclosure includes a memory that stores a command to be executed by a computer and a processor that is configured to execute the stored command. The processor extracts at least one reference part that is common in a first image and a second image, from each of the first image and the second image, the first image and the second image being images of a photographic subject at different imaging times, derives first position information indicating a relative position of at least one abnormal part specified in the first image, relative to the at least one reference part in the first image, derives second position information indicating a relative position of at least one abnormal part specified in the second image, relative to the at least one reference part in the second image, and associates, on the basis of a difference between the first position information and the second position information, the abnormal part included in the first image and the abnormal part included in the second image with each other.

According to the present disclosure, between images at different imaging times, matching of abnormal parts included in the images can be performed accurately with a small calculation amount.

DESCRIPTION OF THE PREFERRED EMBODIMENTS

Figure 1:
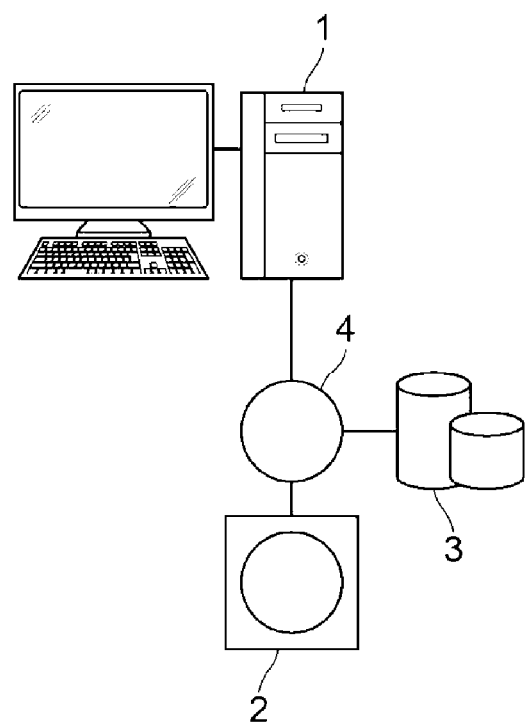
FIG. 1 is a hardware configuration diagram illustrating an overview of a diagnosis supporting system to which a matching apparatus according to an embodiment of the present disclosure is applied.

Now, an embodiment of the present disclosure will be described with reference to the drawings. FIG. 1 is a hardware configuration diagram illustrating an overview of a diagnosis supporting system to which a matching apparatus according to the embodiment of the present disclosure is applied. As illustrated in FIG. 1, in this system, a matching apparatus 1 according to this embodiment, a three-dimensional imaging apparatus 2, and an image storing server 3 are connected in a communicable state via a network 4.

The three-dimensional imaging apparatus 2 is an apparatus that generates a three-dimensional image representing a part to be a diagnosis target of a photographic subject by imaging the part and is, specifically, a CT apparatus, an MRI apparatus, a PET (Positron Emission Tomography) apparatus, or the like. The three-dimensional image generated by the three-dimensional imaging apparatus 2 is transmitted to the image storing server 3 and stored therein. Note that, in this embodiment, the part to be the diagnosis target of the photographic subject is a liver, the three-dimensional imaging apparatus 2 is a CT apparatus, and the three-dimensional image is a CT image of the abdomen of the photographic subject.

The image storing server 3 is a computer that saves and manages various types of data and includes an external mass storage device and database management software. The image storing server 3 communicates with other apparatuses via the wired or wireless network 4 to transmit and receive image data or the like. Specifically, the image storing server 3 acquires image data of the three-dimensional image or the like generated by the three-dimensional imaging apparatus 2 via the network and saves the image data in a recording medium, such as the external mass storage device, to manage the image data. Note that the form of storage of the image data and communication between the apparatuses via the network 4 conform to a protocol such as DICOM (Digital Imaging and Communication in Medicine). In addition, a tag based on the DICOM standard is added to the three-dimensional image. The tag includes the name of a patient, information indicating an imaging apparatus, an imaging date and time, and information on an imaging part or the like.

The matching apparatus 1 is implemented as one computer in which a matching program according to the present disclosure is installed. The computer may be a work station or personal computer that is directly operated by a physician who makes a diagnosis or may be a server computer that is connected to the work station or personal computer via a network. The matching program is stored in a storage device of the server computer that is connected to the network or in a network storage in an externally accessible state, and is, in response to a request, downloaded to and installed in a computer used by the physician. Alternatively, the matching program is recorded on a recording medium such as a DVD (Digital Versatile Disc), or a CD-ROM (Compact Disc Read Only Memory), distributed, and installed in a computer from the recording medium.

Figure 2:
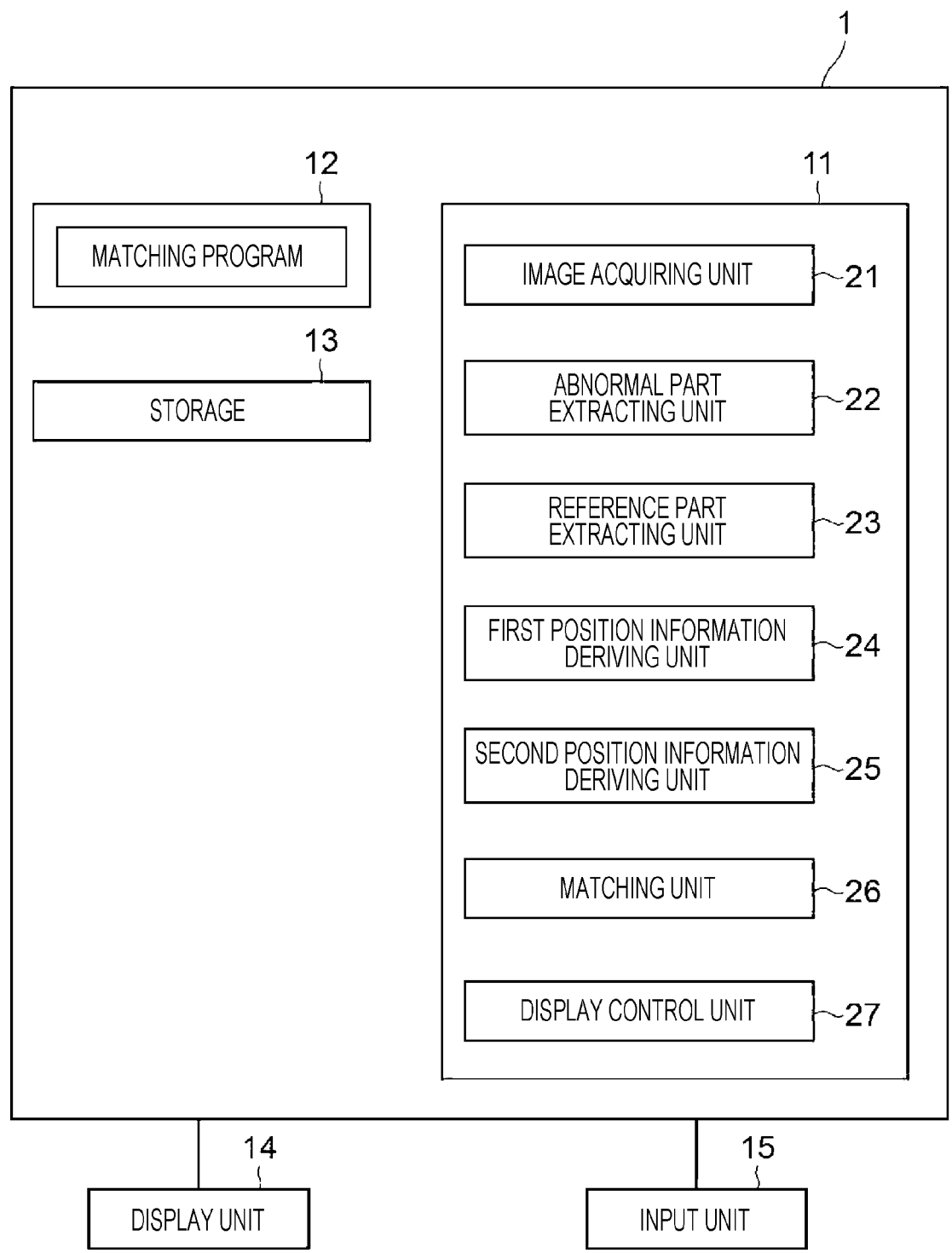
FIG. 2 is a diagram illustrating a schematic configuration of the matching apparatus according to the embodiment, implemented by a computer in which a matching program is installed.

FIG. 2 is a diagram illustrating a schematic configuration of the matching apparatus implemented as a computer in which the matching program is installed. As illustrated in FIG. 2, the matching apparatus 1 includes, as a standard work station configuration, a CPU 11, a memory 12, and a storage 13. In addition, a display unit 14 such as a liquid crystal display and an input unit 15 such as a mouse or a keyboard are connected to the matching apparatus 1. Note that a touch panel serving as both the display unit 14 and the input unit 15 may also be used.

The storage 13 stores various types of information including a three-dimensional image acquired from the image storing server 3 via the network 4 and an image generated by processes in the matching apparatus 1.

In addition, the memory 12 stores the matching program. The matching program defines, as processes to be executed by the CPU 11, an image acquiring process of acquiring a first three-dimensional image S1 and a second three-dimensional image S2 of the same photographic subject at different imaging times, an abnormal part extracting process of extracting at least one abnormal part from each of the first three-dimensional image S1 and the second three-dimensional image S2, a reference part extracting process of extracting at least one reference part that is common in the first three-dimensional image S1 and the second three-dimensional image S2 from each of the first three-dimensional image S1 and the second three-dimensional image S2, a first position information deriving process of deriving first position information indicating a relative position of the at least one abnormal part specified in the first three-dimensional image S1, relative to the at least one reference part in the first three-dimensional image S1, a second position information deriving process of deriving second position information indicating a relative position of the at least one abnormal part specified in the second three-dimensional image S2, relative to the at least one reference part in the second three-dimensional image S2, a matching process of associating the abnormal part included in the first three-dimensional image S1 and the abnormal part included in the second three-dimensional image S2 with each other on the basis of a difference between the first position information and the second position information, and a display control process of displaying, on the display unit 14, the first three-dimensional image S1 and the second three-dimensional image S2 in which the associated abnormal parts are emphasized. Note that the first three-dimensional image S1 is an example of a first image, and the second three-dimensional image S2 is an example of a second image.

By the CPU 11 executing these processes in accordance with the program, the computer functions as an image acquiring unit 21, an abnormal part extracting unit 22, a reference part extracting unit 23, a first position information deriving unit 24, a second position information deriving unit 25, a matching unit 26, and a display control unit 27.

The image acquiring unit 21 acquires the first three-dimensional image S1 and the second three-dimensional image S2 of the same photographic subject at different imaging times from the image storing server 3 through an interface (not illustrated) connected to the network. In this embodiment, the first three-dimensional image S1 is, but not limited to, a three-dimensional image acquired by the most recent inspection, and the second three-dimensional image S2 is, but not limited to, a three-dimensional image acquired by the last-time inspection. Note that, in a case where the first and second three-dimensional images S1 and S2 are already stored in the storage 13, the image acquiring unit 21 may acquire the first and second three-dimensional images S1 and S2 from the storage 13.

The abnormal part extracting unit 22 extracts at least one abnormal part from each of the first three-dimensional image S1 and the second three-dimensional image S2. In this embodiment, the diagnosis target part is a liver. Thus, the abnormal part extracting unit 22 first extracts a liver region from each of the first and second three-dimensional images S1 and S2. As a method of extracting the liver region, any given method can be used, such as a method of using a histogram of a pixel value of a three-dimensional image described in JP2002-345807A or a method of estimating the range of a CT value where the liver is present in the first and second three-dimensional images S1 and S2, of performing a threshold process by using the value, and of applying a morphology filter to the extracted region. In addition, the abnormal part extracting unit 22 may include a trained model that has been subjected to machine learning so as to extract the liver region and may extract the liver region by using the trained model. Note that the method of extracting the liver region is not limited to these methods, and any given method can be used.

Figure 3:
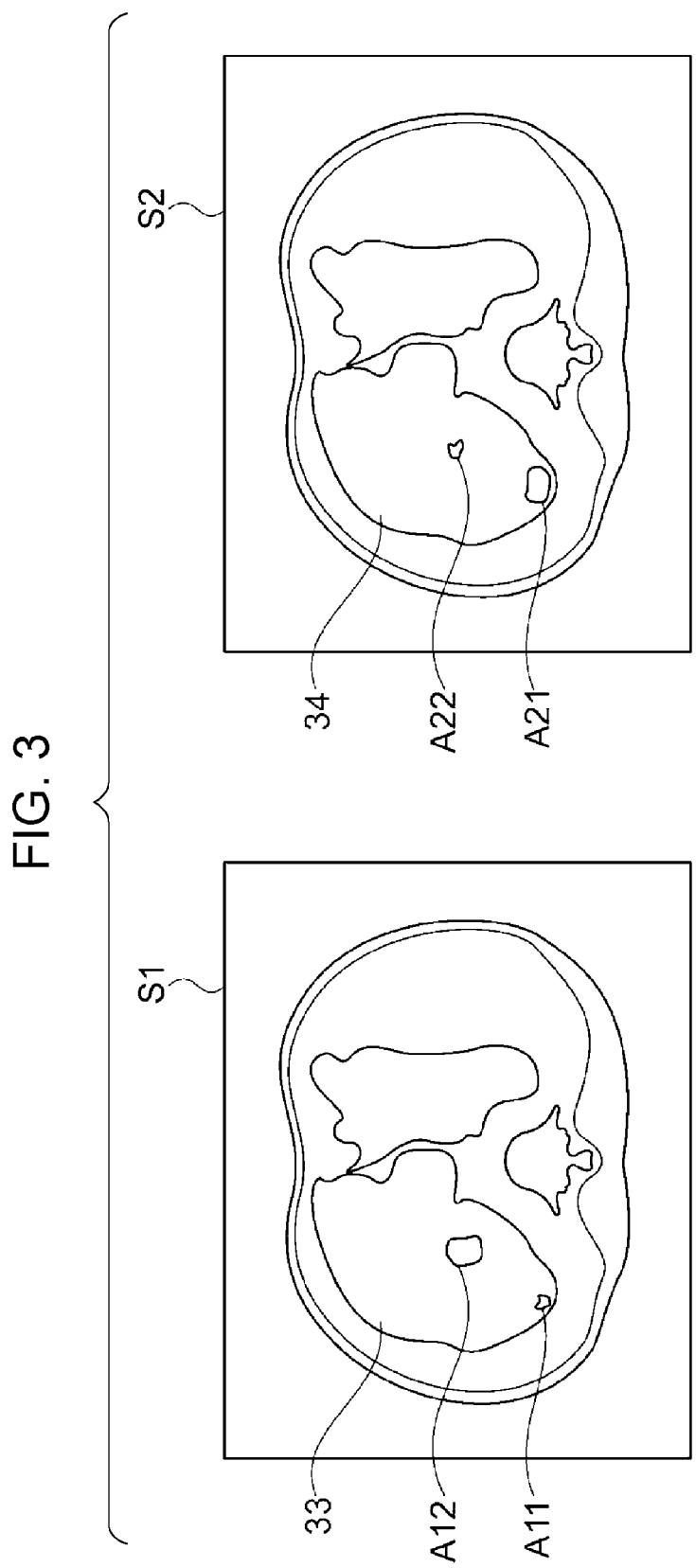
FIG. 3 is a diagram illustrating first and second three-dimensional images from which abnormal parts are extracted.

In addition, the abnormal part extracting unit 22 extracts an abnormal part such as a tumor included in the extracted liver region. In this embodiment, the abnormal part extracting unit 22 includes a trained model that has been subjected to machine learning so as to extract the abnormal part such as a tumor included in the liver. By using the trained model that has been subjected to machine learning in this manner, the abnormal part extracting unit 22 extracts the abnormal part from the liver region. FIG. 3 is a diagram illustrating the first and second three-dimensional images from which abnormal parts are extracted. Note that FIG. 3 illustrates corresponding tomographic images of one tomographic surface in the first and second three-dimensional images S1 and S2 for easy illustration and description. As illustrated in FIG. 3, two abnormal parts A11 and A12 are extracted from a liver region 33 in the first three-dimensional image S1, and two abnormal parts A21 and A22 are extracted from a liver region 34 in the second three-dimensional image S2.

Note that the extraction of the abnormal part by the abnormal part extracting unit 22 is not limited to the configuration of including the trained model. The abnormal part extracting unit 22 may analyze an image by using CAD to extract the abnormal part.

The reference part extracting unit 23 extracts at least one reference part that is common in the first three-dimensional image S1 and the second three-dimensional image S2 from each of the first and second three-dimensional images S1 and S2. The reference part extracting unit 23 may extract a plurality of reference parts, each of which is the reference part. Here, the reference part is a part whose position, size, shape, and the like do not change over time. In this embodiment, the first and second three-dimensional images S1 and S2 are CT images of the abdomen of the same photographic subject. The abdomen includes the spine. Thus, in this embodiment, at least one vertebra in the spine is extracted as the reference part.

Here, in the CT image, CT values differ between a bone and soft tissue such as an organ. Thus, in this embodiment, a CT value is subjected to a threshold process, and thereby, a bone region is extracted from each of the first and second three-dimensional images S1 and S2. Furthermore, the extracted bone region is subjected to, for example, template matching using a template having a vertebra shape, and thereby, the vertebra is extracted. Note that the three-dimensional images S1 and S2 include a plurality of vertebras, and thus, the reference part extracting unit 23 extracts all of the plurality of vertebras. In addition, the vertebras may be extracted by using a trained model that has been subjected to learning so as to extract the vertebras.

Figure 4:
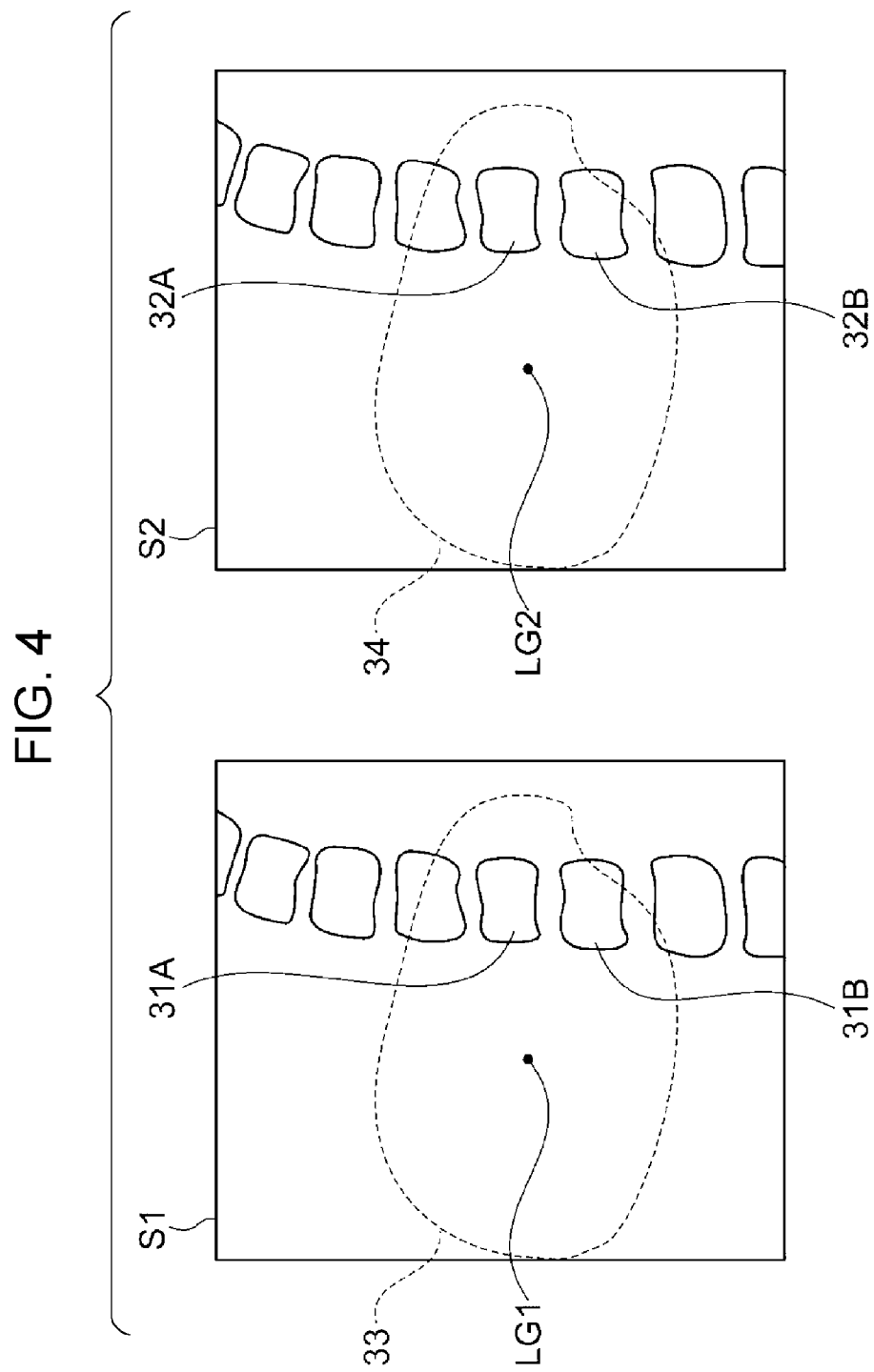
FIG. 4 is a diagram for describing specifying of vertebras that are reference parts.

The reference part extracting unit 23 extracts two vertebras near the liver as reference parts from among the plurality of vertebras included in the first and second three-dimensional images S1 and S2. FIG. 4 is a diagram for describing specifying of the vertebras that are the reference parts. Note that FIG. 4 is a view of the first and second three-dimensional images S1 and S2 seen in the coronal direction. As illustrated in FIG. 4, from each of the first and second three-dimensional images S1 and S2, a plurality of vertebras are extracted. The reference part extracting unit 23 derives center-of-gravity positions LG1 and LG2 of the liver regions 33 and 34 extracted by the abnormal part extracting unit 22 described above and extracts two vertebras near the derived center-of-gravity positions LG1 and LG2 as reference parts 31A, 31B, 32A, and 32B.

Figure 5:
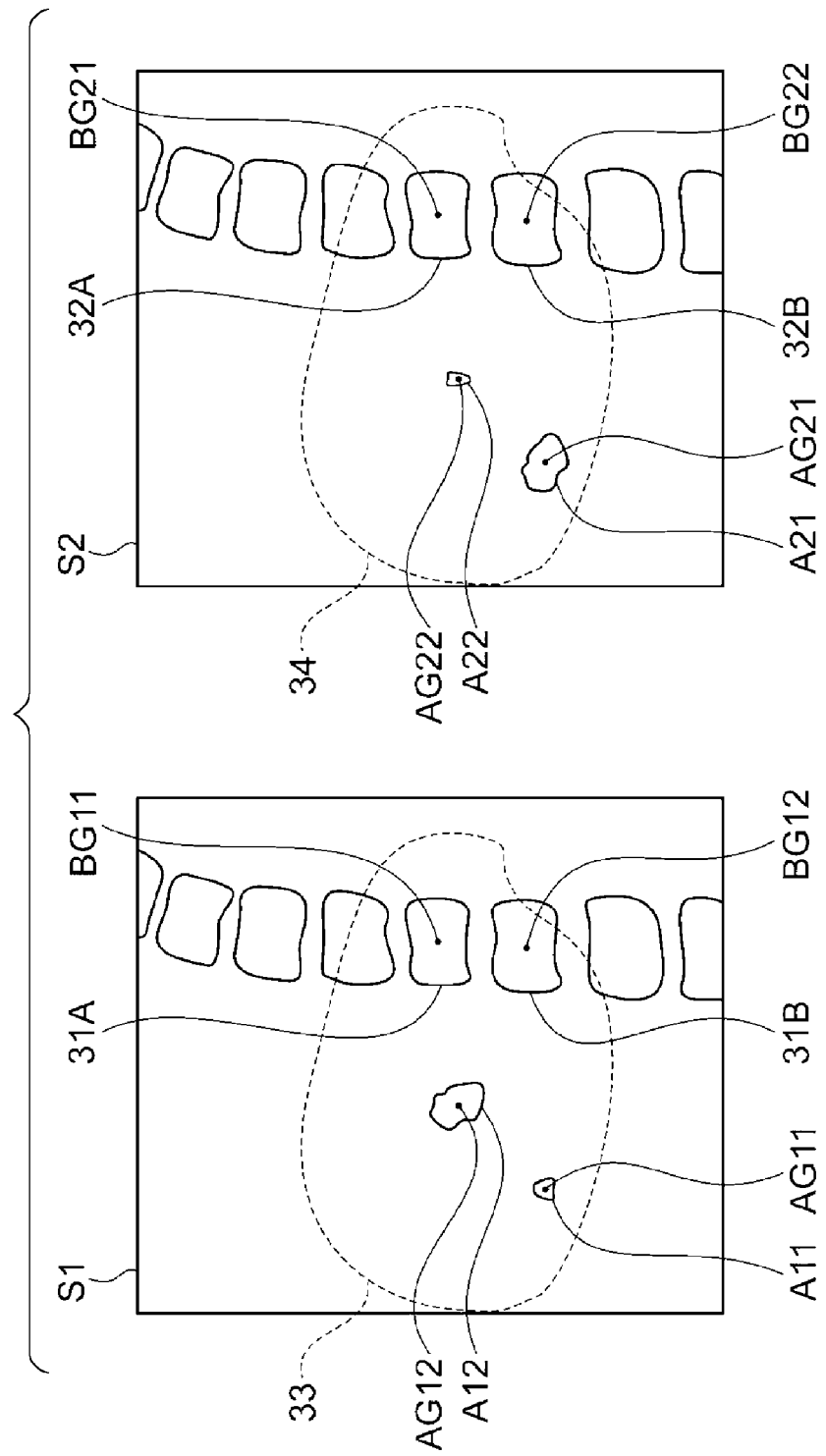
FIG. 5 is a diagram for describing deriving of center-of-gravity positions of the reference parts and the abnormal parts.

The first position information deriving unit 24 derives first position information indicating relative positions of the abnormal parts A11 and A12 specified in the first three-dimensional image S1, relative to the reference parts 31A and 31B in the first three-dimensional image S1. Thus, as illustrated in FIG. 5, the first position information deriving unit 24 derives center-of-gravity positions BG11 and BG12 of the vertebras that are the reference parts 31A and 31B. The first position information deriving unit 24 also derives center-of-gravity positions AG11 and AG12 of the abnormal parts A11 and A12 extracted in the first three-dimensional image S1.

Figure 6:
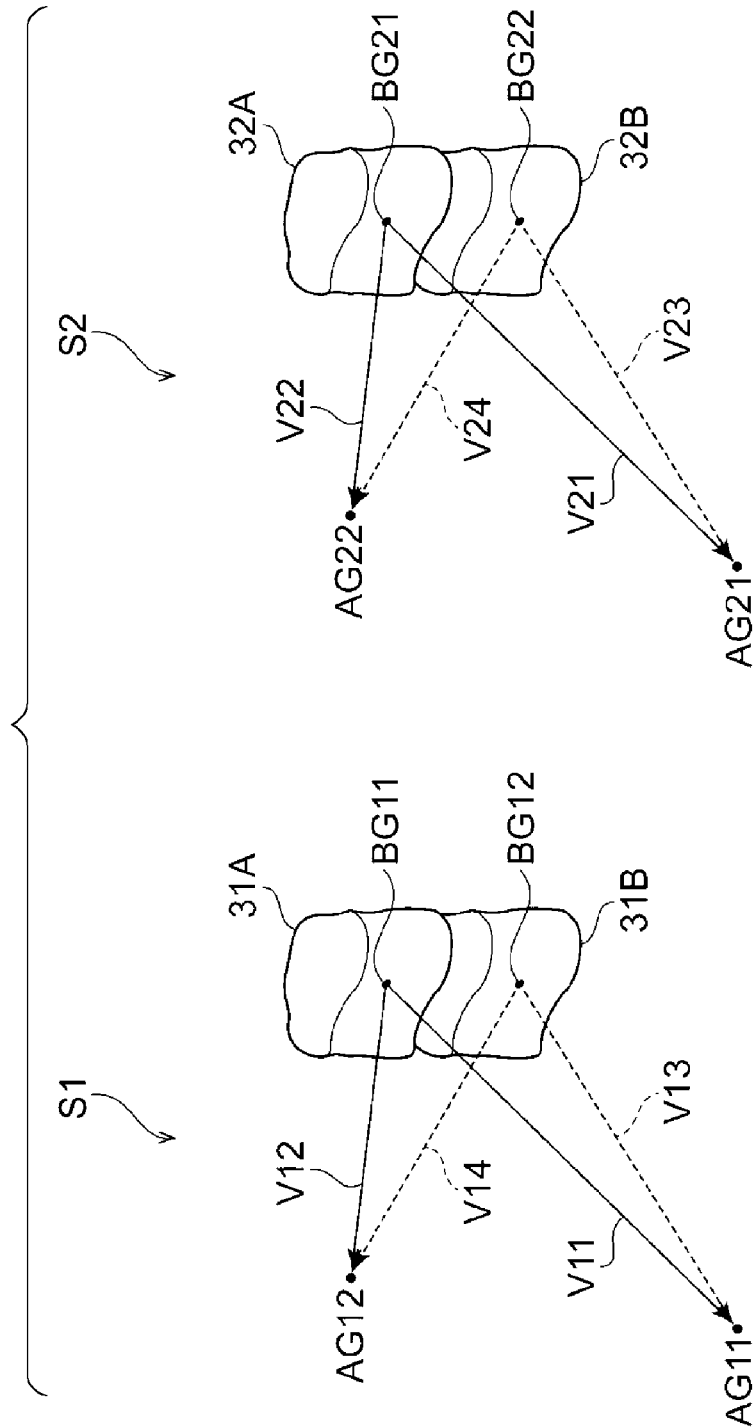
FIG. 6 is a diagram for describing deriving of first and second position information.

Subsequently, as illustrated in FIG. 6, the first position information deriving unit 24 derives, as the first position information, a vector V11 from the center-of-gravity position BG11 toward the center-of-gravity position AG11 of the abnormal part A11, a vector V12 from the center-of-gravity position BG11 toward the center-of-gravity position AG12 of the abnormal part A12, a vector V13 from the center-of-gravity position BG12 toward the center-of-gravity position AG11 of the abnormal part A11, and a vector V14 from the center-of-gravity position BG12 toward the center-of-gravity position AG12 of the abnormal part A12.

The second position information deriving unit 25 derives second position information indicating relative positions of the abnormal parts A21 and A22 specified in the second three-dimensional image S2, relative to the reference parts 32A and 32B in the second three-dimensional image S2. Thus, as illustrated in FIG. 5, the second position information deriving unit 25 derives center-of-gravity positions BG21 and BG22 of the vertebras that are the reference parts 32A and 32B. The second position information deriving unit 25 also derives center-of-gravity positions AG21 and AG22 of the abnormal parts A21 and A22 extracted in the second three-dimensional image S2.

Subsequently, as illustrated in FIG. 6, the second position information deriving unit 25 derives, as the second position information, a vector V21 from the center-of-gravity position BG21 toward the center-of-gravity position AG21 of the abnormal part A21, a vector V22 from the center-of-gravity position BG21 toward the center-of-gravity position AG22 of the abnormal part A22, a vector V23 from the center-of-gravity position BG22 toward the center-of-gravity position AG21 of the abnormal part A21, and a vector V24 from the center-of-gravity position BG22 toward the center-of-gravity position AG22 of the abnormal part A22.

Figure 7:
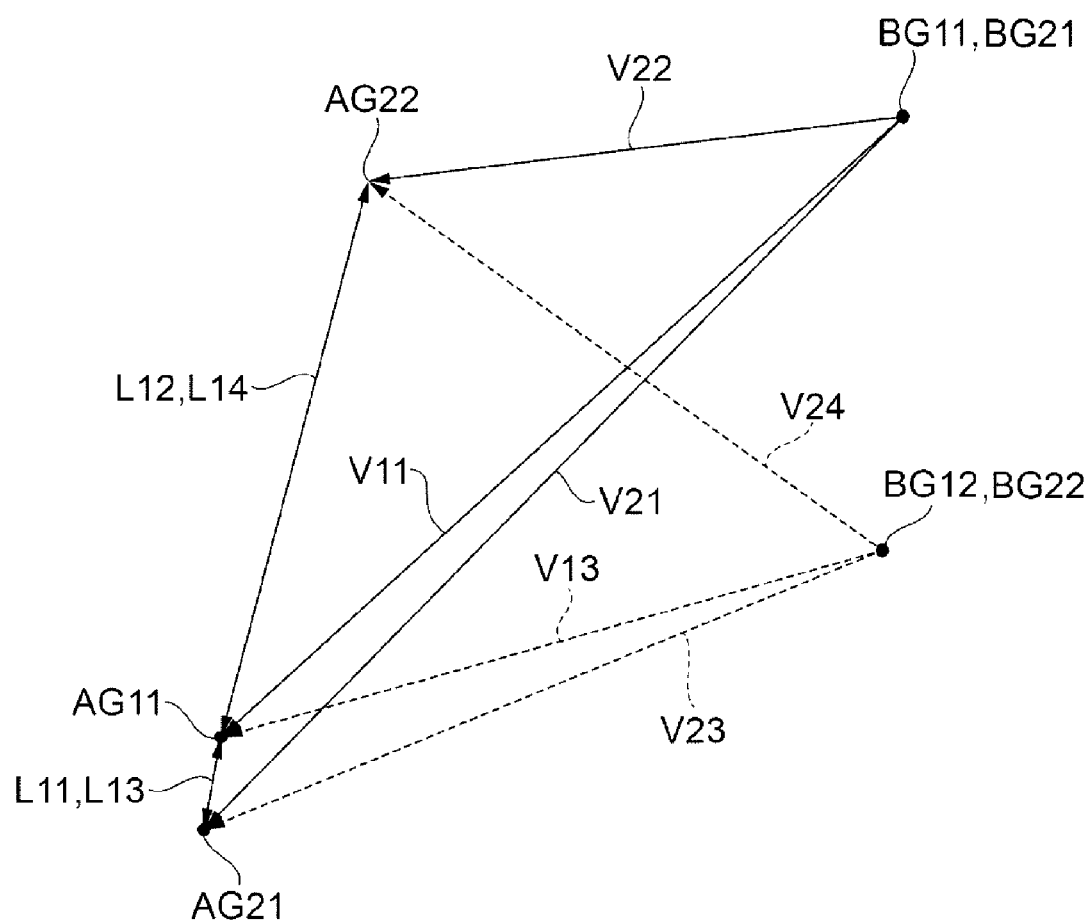
FIG. 7 is a diagram for describing deriving of the distance between the abnormal part included in the first three-dimensional image and the abnormal part included in the second three-dimensional image.

On the basis of a difference between the first position information and the second position information, the matching unit 26 performs a matching process of associating the abnormal part included in the first three-dimensional image S1 and the abnormal part included in the second three-dimensional image S2 with each other. Thus, by using the first position information and the second position information, the matching unit 26 derives the distance between the abnormal part included in the first three-dimensional image S1 and the abnormal part included in the second three-dimensional image S2. That is, the matching unit 26 derives, as the difference between the first position information and the second position information, the distance between the abnormal part included in the first three-dimensional image S1 and the abnormal part included in the second three-dimensional image S2. FIG. 7 is a diagram for describing deriving of the distance between the abnormal part included in the first three-dimensional image S1 and the abnormal part included in the second three-dimensional image S2.

Here, as described above, the vectors V11 to V14 derived in the first three-dimensional image S1 and the vectors V21 to V24 derived in the second three-dimensional image S2 can be regarded as being on the same coordinate system. Thus, for the abnormal part A11 included in the first three-dimensional image S1, on the basis of the vector V11 and the vectors V21 and V22, the matching unit 26 derives distances L11 and L12 between the center-of-gravity position AG11 of the abnormal part A11 and the center-of-gravity positions AG21 and AG22 of the abnormal parts A21 and A22 included in the second three-dimensional image S2 according to the following Formulas (1) and (2). In addition, on the basis of the vector V13 and the vectors V23 and V24, the matching unit 26 derives distances L13 and L14 between the center-of-gravity position AG11 of the abnormal part A11 and the center-of-gravity positions AG21 and AG22 of the abnormal parts A21 and A22 included in the second three-dimensional image S2 according to the following Formulas (3) and (4). Note that, in formulas (1) to (4), (x11, y11, z11) is the vector V11, (x21, y21, z21) is the vector V21, (x22, y22, z22) is the vector V22, (x13, y13, z13) is the vector V13, (x23, y23, z23) is the vector V23, and (x24, y24, z24) is the vector V24.

$$L11 = \sqrt{\{(x11-x21)^2 + (y11-y21)^2 + (z11-z21)^2\}} \quad (1)$$

$$L12 = \sqrt{\{(x11-x21)^2 + (y11-y22)^2 + (z11-z22)^2\}} \quad (2)$$

$$L13 = \sqrt{\{(x13-x23)^2 + (y13-y23)^2 + (z13-z23)^2\}} \quad (3)$$

$$L14 = \sqrt{\{(x13-x24)^2 + (y13-y24)^2 + (z13-z24)^2\}} \quad (4)$$

Subsequently, the matching unit 26 compares the distances L11, L12, L13, and L14 with a predetermined threshold Th1. For example, the threshold Th1 may be, but is not limited to, a value of about 10 pixels in the three-dimensional images S1 and S2. Note that a value in mm or the like may also be used as the threshold Th1 instead of pixels. Subsequently, abnormal parts between which the distance is less than the threshold Th1 are associated with each other. As for the abnormal part A11, the distances L11 and L13 are less than the threshold Th1. Thus, the matching unit 26 associates the abnormal part A11 included in the first three-dimensional image S1 and the abnormal part A21 included in the second three-dimensional image S2 with each other. On the other hand, in a case where a plurality of abnormal parts are present between which the distance is less than the threshold Th1, the closest abnormal parts may be associated with each other.

On the other hand, as for the abnormal part A12 included in the first three-dimensional image S1, although omitted from the illustration, on the basis of the vector V12 and the vectors V21 and V22, the matching unit 26 derives distances L21 and L22 between the center-of-gravity position AG12 of the abnormal part A12 and the center-of-gravity positions AG21 and AG22 of the abnormal parts A21 and A22 included in the second three-dimensional image S2 according to the following Formulas (5) and (6). In addition, on the basis of the vector V14 and the vectors V23 and V24, the matching unit 26 derives distances L23 and L24 between the center-of-gravity position AG12 of the abnormal part A12 and the center-of-gravity positions AG21 and AG22 of the abnormal parts A21 and A22 included in the second three-dimensional image S2 according to the following Formulas (7) and (8).

$$L21=\sqrt{\{(x12-x21)^2+(y12-y21)^2+(z12-z21)^2\}} \quad (5)$$

$$L22=\sqrt{\{(x12-x22)^2+(y12-y22)^2+(z12-z22)^2\}} \quad (6)$$

$$L23=\sqrt{\{(x14-x23)^2+(y14-y23)^2+(z14-z23)^2\}} \quad (7)$$

$$L24=\sqrt{\{(x14-x24)^2+(y14-y24)^2+(z14-z24)^2\}} \quad (8)$$

Subsequently, the matching unit 26 compares the distances L21, L22, L23, and L24 with the predetermined threshold Th1. Subsequently, abnormal parts between which the distance is less than the threshold Th1 are associated with each other. As for the abnormal part A12, the distances L22 and L24 are less than the threshold Th1. Thus, the matching unit 26 associates the abnormal part A12 included in the first three-dimensional image S1 and the abnormal part A22 included in the second three-dimensional image S2 with each other.

Figure 8:
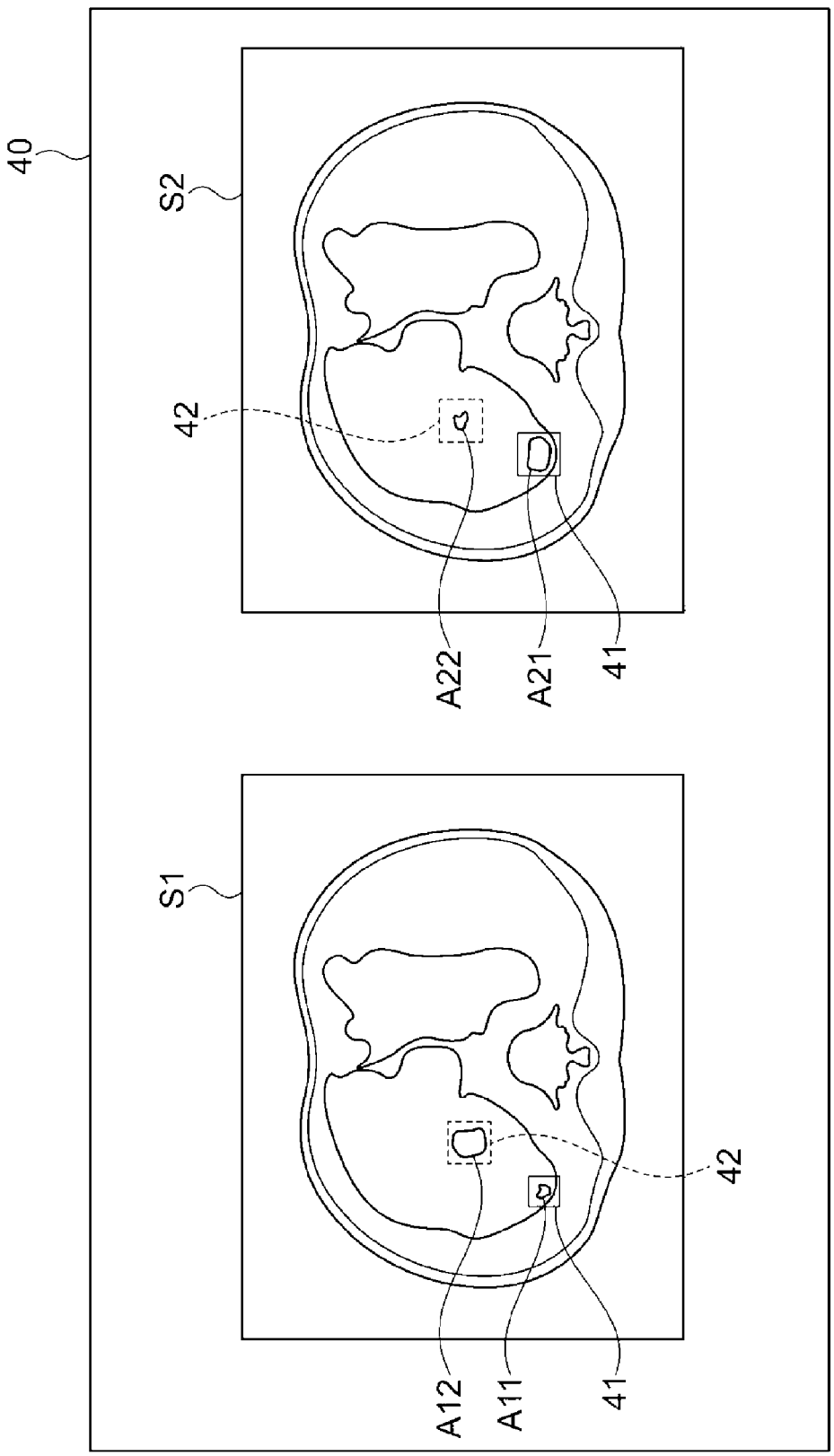
FIG. 8 is a diagram illustrating display screens of the first three-dimensional image and the second three-dimensional image that are displayed on a display unit.

The display control unit 27 displays, on the display unit 14, the first three-dimensional image S1 and the second three-dimensional image S2 in which the associated abnormal parts are emphasized. FIG. 8 is a diagram illustrating display screens of the first three-dimensional image S1 and the second three-dimensional image S2 that are displayed on the display unit 14. As illustrated in FIG. 8, tomographic images of a corresponding tomographic surface of the first three-dimensional image S1 and the second three-dimensional image S2 are displayed on a display screen 40. In addition, in FIG. 8, association between the abnormal part A11 included in the first three-dimensional image S1 and the abnormal part A21 included in the second three-dimensional image S2 is emphasized by adding a solid line frame 41 to the abnormal parts A11 and A21. In addition, association between the abnormal part A12 included in the first three-dimensional image S1 and the abnormal part A22 included in the second three-dimensional image S2 is emphasized by adding a broken line frame 42 to the abnormal parts A12 and A22.

Figure 9:
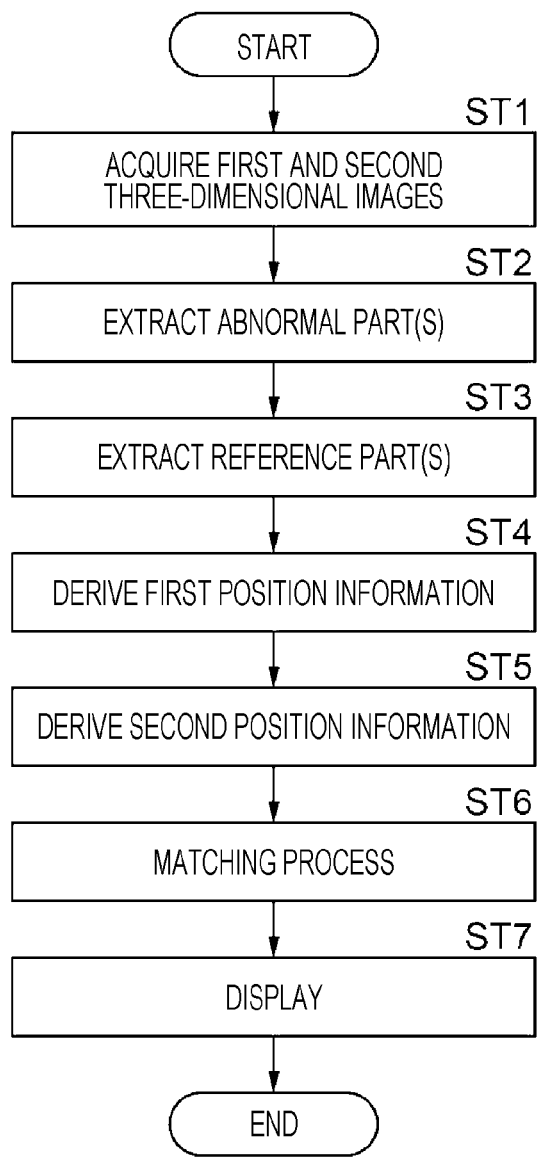
FIG. 9 is a flowchart illustrating processes performed in the embodiment.

Subsequently, processes performed in this embodiment will be described. FIG. 9 is a flowchart illustrating the processes performed in this embodiment. First, the image acquiring unit 21 acquires the first and second three-dimensional images S1 and S2 that are diagnosis targets from the image storing server 3 (step ST1). Subsequently, the abnormal part extracting unit 22 extracts at least one abnormal part from each of the first three-dimensional image S1 and the second three-dimensional image S2 (step ST2). Furthermore, the reference part extracting unit 23 extracts at least one reference part that is common in the first three-dimensional image S1 and the second three-dimensional image S2 from each of the first three-dimensional image S1 and the second three-dimensional image S2 (step ST3). Note that the process in step ST3 may be performed prior to the process in step ST2, or the process in step ST2 and the process in step ST3 may be performed in parallel.

Subsequently, the first position information deriving unit 24 derives the first position information indicating the relative position of the at least one abnormal part specified in the first three-dimensional image S1, relative to the at least one reference part in the first three-dimensional image S1 (step ST4). In addition, the second position information deriving unit 25 derives the second position information indicating the relative position of the at least one abnormal part specified in the second three-dimensional image S2, relative to the at least one reference part in the second three-dimensional image S2 (step ST5). Subsequently, on the basis of the difference between the first position information and the second position information, the matching unit 26 associates the abnormal part included in the first three-dimensional image S1 and the abnormal part included in the second three-dimensional image S2 with each other (matching process; step ST6). Furthermore, the display control unit 27 displays, on the display unit 14, the first three-dimensional image S1 and the second three-dimensional image S2 in which the associated abnormal parts are emphasized (step ST7), and the process ends.

In this manner, in this embodiment, on the basis of the difference between the first position information and the second position information, the abnormal part included in the first three-dimensional image S1 and the abnormal part included in the second three-dimensional image S2 are associated with each other. Thus, the calculation amount for matching the abnormal parts can be reduced. In addition, even in a case where the first three-dimensional image S1 and the second three-dimensional image S2 are acquired by different imaging methods, such as a case where the first three-dimensional image S1 is acquired by a CT apparatus and the second three-dimensional image S2 is acquired by an MRI apparatus, since the abnormal parts are associated with each other on the basis of the difference between the first position information and the second position information, the accuracy at the time of the association is not low compared with that of the method of the related art. Thus, according to this embodiment, between images at different imaging times, matching of the abnormal parts included in the images can be performed accurately with a small calculation amount.

Figure 10:
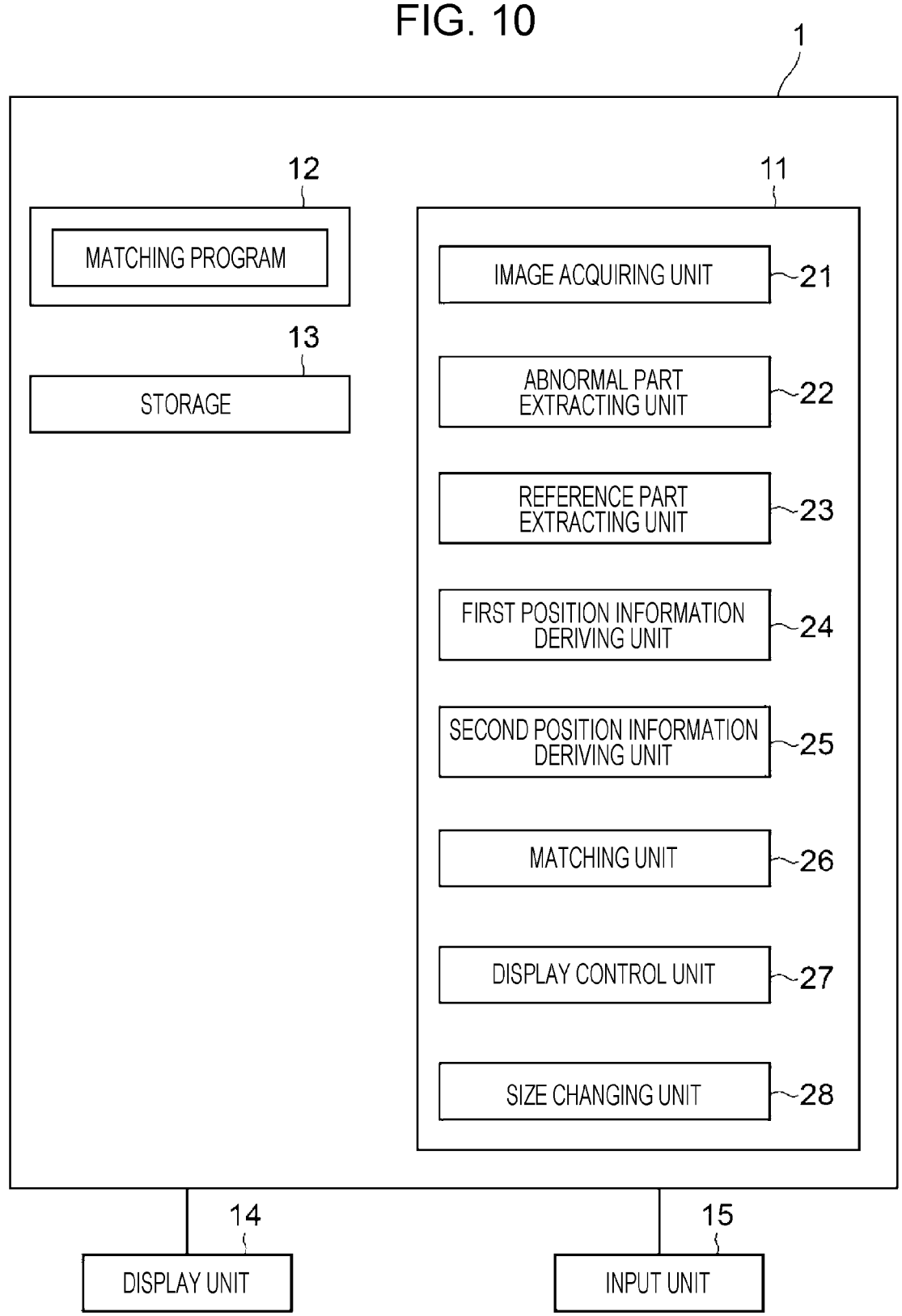
FIG. 10 is a diagram illustrating a schematic configuration of a matching apparatus according to another embodiment.

Note that, in the above embodiment, if the imaging method differs, or if the imaging magnification differs, vertebras included in the first three-dimensional image S1 and the second three-dimensional image S2, that is, the reference parts, may differ in size in some cases. In such a case, it is not possible for the matching unit 26 to derive the difference between the first position information and the second position information accurately. Thus, as illustrated in FIG. 10, the matching apparatus 1 may further include a size changing unit 28 for making the size of the reference part included in the first three-dimensional image S1 and the size of the reference part included in the second three-dimensional image S2 correspond to each other. In this case, the size of a vertebra extracted by the reference part extracting unit 23 from the first three-dimensional image S1 and the size of a vertebra extracted by the reference part extracting unit 23 from the second three-dimensional image S2 may be compared with each other, and, if the sizes are different, the size changing unit 28 may change the size of the first three-dimensional image S1 so that the size of the reference part extracted from the first three-dimensional image S1 can correspond to the size of the reference part extracted from the second three-dimensional image S2. Note that the size changing unit 28 may also change the size of the second three-dimensional image S2 so that the size of the reference part extracted from the second three-dimensional image S2 can correspond to the size of the reference part extracted from the first three-dimensional image S1.

In this case, on the basis of the first three-dimensional image S1 that is subjected to size changing and the second three-dimensional image S2, by deriving the first position information and the second position information, the matching unit 26 can derive the difference between the first position information and the second position information accurately. Thus, matching between the abnormal parts included in the first three-dimensional image S1 and the second three-dimensional image S2 can be performed more accurately.

In addition, although the matching apparatus 1 includes the abnormal part extracting unit 22 in the above embodiment, the present disclosure is not limited to this. A process of extracting an abnormal part may be performed by an external apparatus other than the matching apparatus 1 according to the embodiment. In this case, the image acquiring unit 21 acquires information indicating the extracted abnormal part along with the first and second three-dimensional images S1 and S2.

In addition, although the diagnosis target part is a liver in the above embodiment, the present disclosure is not limited to this. The diagnosis target part may be a part other than a liver, such as a heart, a blood vessel, a lung, or a bronchus, in the chest and abdomen of a human body. The diagnosis target part may also be a brain. In this case, a three-dimensional image is an image of the head of a photographic subject. In this case, the skull may be used as the reference part.

In addition, although vertebras constituting the spine are extracted as the reference parts in the above embodiment, the present disclosure is not limited to this. A bone other than the vertebras, such as a rib, and also, a part whose position, size, and shape do not change over time may also be used as the reference part.

In addition, although the plurality of reference parts are extracted in the above embodiment, the present disclosure is not limited to this. Only a single reference part may also be used.

In addition, although the distance between the abnormal part included in the first three-dimensional image S1 and the abnormal part included in the second three-dimensional image S2 are derived as the difference on the basis of the first position information and the second position information in the above embodiment, the present disclosure is not limited to this. For example, the absolute value of a difference of the vectors, which are the first position information and the second position information, may also be derived as the difference.

Furthermore, in the above embodiment, as a hardware structure of processing units that perform various processes such as the image acquiring unit 21, the abnormal part extracting unit 22, the reference part extracting unit 23, the first position information deriving unit 24, the second position information deriving unit 25, the matching unit 26, the display control unit 27, and the size changing unit 28, any of the following various processors can be used. The various processors include, as described above, in addition to a CPU that is a general-purpose processor functioning as various processing units by executing software (programs), a programmable logic device (PLD) that is a processor in which the circuit configuration is changeable after manufacture, such as an FPGA (Field Programmable Gate Array), a dedicated electric circuit that is a processor having a circuit configuration that is specially designed to execute specific processing, such as an ASIC (Application Specific Integrated Circuit), and the like.

One processing unit may be constituted by one of these various processors, or may be constituted by constituted by a combination of two or more processors of the same type or different types (e.g., a combination of a plurality of FPGAs or a combination of a CPU and an FPGA). In addition, a plurality of processing units may be constituted by one processor.

As a first example for constituting a plurality of processing units as one processor, one or more CPUs and software may be combined to constitute one processor, and this processor may function as a plurality of processing units, as typified by a computer such as a client or a server. As a second example, a processor may be used that implements the functions of the entire system including a plurality of processing units as one IC (Integrated Circuit) chip, as typified by a system on chip (SoC) or the like. In this manner, various processing units are constituted by one or more of the above various processors as a hardware structure.

Furthermore, as the hardware structure of these various processors, more specifically, an electric circuit (Circuitry) in which circuit elements such as semiconductor elements are combined can be used.

REFERENCE SIGNS LIST

1 matching apparatus
2 three-dimensional imaging apparatus
3 image storing server
4 network
11 CPU
12 memory
13 storage
14 display unit
15 input unit
21 image acquiring unit
22 abnormal part extracting unit
23 reference part extracting unit
24 first position information deriving unit
25 second position information deriving unit
26 matching unit
27 display control unit
28 size changing unit
31A, 31B, 32A, 32B reference part 33, 34 liver region
40 display screen
41 solid line frame
42 broken line frame
A11, A12, A21, A22 abnormal part
AG11, AG12, AG21, AG22 center of gravity of abnormal part
BG11, BG12, BG21, BG22 center of gravity of reference part
LG1, LG2 center of gravity of liver region
S1 first three-dimensional image
S2 second three-dimensional image
V11 to V14, V21 to V24 vector

What is claimed is:

1. A matching apparatus comprising a processor that is configured to:
   extract at least one reference part that is common in a first image and a second image, from each of the first image and the second image, the first image and the second image being images of a photographic subject at different imaging times;
   derive first position information indicating a relative position of at least one abnormal part specified in the first image, relative to the at least one reference part in the first image;
   derive second position information indicating a relative position of at least one abnormal part specified in the second image, relative to the at least one reference part in the second image;
   derive, on the basis of the first position information and the second position information, a linear distance between the abnormal part included in the first image and the abnormal part included in the second image; and
   associate, on the basis of the linear distance between the abnormal parts respectively included in the first and second images, the abnormal part included in the first image and the abnormal part included in the second image with each other.

2. The matching apparatus according to claim 1,
   wherein the processor is configured to
   derive, as the first position information, a vector from the reference part toward the abnormal part included in the first image, and
   derive, as the second position information, a vector from the reference part toward the abnormal part included in the second image.

3. The matching apparatus according to claim 1,
   wherein the processor is configured to associate the abnormal part included in the first image and the abnormal part included in the second image with each other for which the linear distance is less than a predetermined threshold.

4. The matching apparatus according to claim 1,
   wherein the processor is configured to extract a plurality of reference parts from each of the first and second images, respectively.

5. The matching apparatus according to claim 1,
   wherein the reference part is a bone.

6. The matching apparatus according to claim 5,
   wherein the bone is a vertebra.

7. The matching apparatus according to claim 1,
   wherein the processor is configured to extract the at least one abnormal part from each of the first image and the second image.

8. The matching apparatus according to claim 1,
   wherein the processor is configured to make a size of the reference part included in the first image and a size of the reference part included in the second image correspond to each other in a case where the size of the reference part included in the first image and the size of the reference part included in the second image are different from each other.

9. The matching apparatus according to claim 1,
   wherein the processor is configured to display, on a display, the first image and the second image in which the associated abnormal parts are emphasized.

10. A matching method comprising:
    extracting at least one reference part that is common in a first image and a second image, from each of the first image and the second image, the first image and the second image being images of a photographic subject at different imaging times;
    deriving first position information indicating a relative position of at least one abnormal part specified in the first image, relative to the at least one reference part in the first image;
    deriving second position information indicating a relative position of at least one abnormal part specified in the second image, relative to the at least one reference part in the second image;
    deriving, on the basis of the first position information and the second position information, a linear distance between the abnormal part included in the first image and the abnormal part included in the second image; and
    associating, on the basis of the linear distance between the abnormal parts respectively included in the first and second images, the abnormal part included in the first image and the abnormal part included in the second image with each other.

11. The matching method according to claim 10,
    wherein the abnormal part included in the first image and the abnormal part included in the second image are associated with each other for which the linear distance is less than a predetermined threshold.

12. A non-transitory computer readable recording medium storing a matching program causing a computer to execute:
    extracting at least one reference part that is common in a first image and a second image, from each of the first image and the second image, the first image and the second image being images of a photographic subject at different imaging times;
    deriving first position information indicating a relative position of at least one abnormal part specified in the first image, relative to the at least one reference part in the first image;
    deriving second position information indicating a relative position of at least one abnormal part specified in the second image, relative to the at least one reference part in the second image;
    deriving, on the basis of the first position information and the second position information, a linear distance between the abnormal part included in the first image and the abnormal part included in the second image; and
    associating, on the basis of the linear distance between the abnormal parts respectively included in the first and second images, the abnormal part included in the first image and the abnormal part included in the second image with each other.

13. The non-transitory computer readable recording medium storing the matching program according to claim 12,
wherein the abnormal part included in the first image and the abnormal part included in the second image are associated with each other for which the linear distance is less than a predetermined threshold.

* * * * *